United States Patent
Brooks et al.

(10) Patent No.: US 7,468,188 B2
(45) Date of Patent: *Dec. 23, 2008

(54) MULTI-STEP THERAPY FOR INJURED MUSCLES

(75) Inventors: Gregory F. Brooks, Irvine, CA (US); Kei R. Aoki, Coto De Caza, CA (US)

(73) Assignee: Allergan, Inc., Irvine, CA (US)

( * ) Notice: Subject to any disclaimer, the term of this patent is extended or adjusted under 35 U.S.C. 154(b) by 88 days.

This patent is subject to a terminal disclaimer.

(21) Appl. No.: 11/507,708

(22) Filed: Aug. 22, 2006

(65) Prior Publication Data

US 2007/0128227 A1   Jun. 7, 2007

Related U.S. Application Data

(63) Continuation of application No. 10/981,212, filed on Nov. 3, 2004, now Pat. No. 7,108,857, which is a continuation of application No. 10/155,925, filed on May 23, 2002, now Pat. No. 6,955,813, which is a continuation of application No. 09/678,189, filed on Oct. 4, 2000, now Pat. No. 6,423,319.

(51) Int. Cl.
*A61K 39/08* (2006.01)
*A61K 38/00* (2006.01)

(52) U.S. Cl. ............. 424/239.1; 424/9.1; 514/12; 530/350; 530/412; 435/69.1; 435/320.1; 435/252.3; 536/23.1

(58) Field of Classification Search ............. 424/239.1, 424/9.1; 514/12; 530/350, 412; 435/69.1, 435/320.1, 252.3; 536/23.1
See application file for complete search history.

(56) References Cited

U.S. PATENT DOCUMENTS

| 5,721,215 | A | 2/1998 | Aoki et al. |
| 6,063,768 | A | 5/2000 | First |
| 6,423,319 | B1 * | 7/2002 | Brooks et al. ............ 424/239.1 |
| 6,447,787 | B1 | 9/2002 | Gassner et al. |
| 6,955,813 | B2 * | 10/2005 | Brooks et al. ............ 424/239.1 |
| 7,108,857 | B2 * | 9/2006 | Brooks et al. ............ 424/239.1 |

FOREIGN PATENT DOCUMENTS

| WO | 9415629 | 7/1994 |
| WO | WO 94/28923 | 12/1994 |
| WO | WO 95/17094 | 7/1995 |
| WO | WO 00/24419 | 5/2000 |

OTHER PUBLICATIONS

Morre, et al.; *Treatment of Chronic Tennis Elbow with Botulinum Toxin*; Lancet, Jun. 14, 1997;349(9067): 1746 (1 pg.); Abstract.
Garrett, JR., et al. The American Journal of Sports Medicine. V.24 No. 8, 1996 S2-S8.
Jarvinen, et al. Current Opinion in Rheumatology, 2000, 12:159-161.
Morre, et al, Lancet 1997:349 (9067): 1746.
Trotter et al., Treatment of Subtotal medial Rectus Myectomy Complicating Functional Endoscopic Sinus Surgery. J. AAPOS 4, 250-253 (Aug). 2000).

* cited by examiner

*Primary Examiner*—Chih-Min Kam
(74) *Attorney, Agent, or Firm*—Claude L. Nassif; Stephen Donovan; Martin Voet

(57) ABSTRACT

Methods for treating an injured muscle by local administration of a neurotoxin, such as a *botulinum* toxin, to promote healing and/or to reduce the pain associated with an injured muscle.

13 Claims, No Drawings

MULTI-STEP THERAPY FOR INJURED MUSCLES

CROSS REFERENCE

This application is a continuation of U.S. application Ser. No. 10/981,212, filed on Nov. 3, 2004, now U.S. Pat. No. 7,108,857, which is a continuation of U.S. application Ser. No. 10/155,925, filed May 23, 2002, now U.S. Pat. No. 6,955,813, which is a continuation of U.S. application Ser. No. 09/678,189, filed Oct. 4, 2000, now U.S. Pat. No. 6,423,319, the disclosures of which are herein incorporated by reference in their entirety.

BACKGROUND

The present invention relates to methods for treating muscle injuries. In particular, the present invention relates to a method for treating an injured muscle by administration of a neurotoxin to the injured muscle.

Injuries to muscles include acute injuries to skeletal muscles such as contusions (bruises), lacerations, ischemia, strains, and complete ruptures. These injuries may cause tremendous pain and can incapacitate the affected person, preventing them from being able to go to work or even to participate in normal daily activities. Of the acute injuries to skeletal muscles, strain (also known as stretch-induced injuries) is most common. For example, strains can account for up to 30% of all injuries treated by occupational or sports medicine professionals. Garrett et al. *Am J Sports Med*, 24(6):S2-S8, 1996.

A muscle strain injury is characterized by a disruption of a muscle-tendon unit. The disruption of the muscle-tendon unit may occur anywhere on the muscle. This type of injury most commonly occurs near the myotendinous junction (MTJ) of the superficial muscles working across two joints, such as the rectus femoris, semitendinousus and gastroenemius muscles.

Muscle strain may result from an eccentric exercise, or uncommon use of the muscle. For example, eccentric contractions employ fewer active motor units to generate higher forces. In such case, the over-extended muscle units experience excessive tension during lengthening. The excessive tension may cause microscopic damages to the contractile element of the muscle, centering on what appears to be random disruptions of the Z-lines. When the muscle is damaged, the affected person may experience a delayed onset muscle soreness, characterized by pain, weakness and a limited range of motion. The pain is most intense for about 1 to 2 days after the muscle injury and the weakness and limited range of motion can last for a week or more. If a minor strain of the skeletal muscles is treated inappropriately, a more serious injury can occur.

There are three classifications of muscle strains, based on the severity of the injury and the nature of the hematoma: (1) mild, (first degree) strain; a tear of a few muscle fibers; minor swelling and discomfort with no or only minimal loss of strength and restriction of movement; (2) moderate, (second degree) strain; a greater damage of muscle fibers with a clear loss of strength, and; (3) severe (third degree) strain; a tear extending across the whole muscle belly, resulting in a total loss of muscle function.

Tearing of the intramuscular blood vessels during muscle strain can often result in a large hematoma. Two different types of hematomas occur in the injured muscle: intramuscular and intermuscular hematomas. The first type, intramuscular hematomas, is limited in size by the intact muscle fascia. There, the extravasation of blood increases the intramuscular pressure, compressing and limiting the size of the hematoma. Such type of hematoma causes pain and loss of function of the muscle. The second type, intermuscular hematomas, develops when the muscle fascia is ruptured and extravasated blood spreads into the intermuscular spaces without significantly increasing the pressure within the muscle. This type of hematoma may not cause significant pain if the pressure within the muscle does not increase.

For treatments of strain injuries, it is critical that the injured muscle be immobilized, especially during the first two to three days after the injury, since mobilization of the injured muscles immediately after the injury often causes re-rupturing at the original injury site. A re-rupturing may lead to more severe injuries, delayed healing and scarring of tissues. Jarvinen et al., *Curr Opin Rheumatol*, vol 12:155-161 (2000).

Re-rupturing of the damaged site may be avoided by immobilizing the injured muscle, preferably immediately after the injury. Immobilization allows the newly formed granulation tissue to reach sufficient tensile strength to withstand the forces created by contracting muscle.

A known method for immobilization of an injured/strained muscle requires use of a physical restraint or cast. For example, a cervical collar can be used to immobilize an injured cervical flexor or extensor. However, the use of a restraint is often cumbersome and uncomfortable. Moreover, for injuries of certain muscle groups, it is not practical or possible to use a physical restraint. For example, it is very difficult to immobilize a strained upper trapezius or gluteus maximus muscle with a restraint.

Botulinum Toxin

The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A ("BoNT/A") is the most lethal natural biological neurotoxin known to man. About 50 picograms of *botulinum* toxin (purified neurotoxin complex) serotype A is a $LD_{50}$ in mice. One unit (U) of *botulinum* toxin is defined as the $LD_{50}$ upon intraperitoneal injection into female Swiss Webster mice weighing 18-20 grams each. Seven immunologically distinct *botulinum* neurotoxins have been characterized, these being respectively *botulinum* neurotoxin serotypes A, B, $C_1$, D, E, F and G each of which is distinguished by neutralization with serotype-specific antibodies. The different serotypes of *botulinum* toxin vary in the animal species that they affect and in the severity and duration of the paralysis they evoke. For example, it has been determined that BoNt/A is 500 times more potent, as measured by the rate of paralysis produced in the rat, than is *botulinum* toxin serotype B (BoNT/B). Additionally, BoNt/B has been determined to be non-toxic in primates at a dose of 480 U/kg which is about 12 times the primate $LD_{50}$ for BoNt/A. *Botulinum* toxin apparently binds with high affinity to cholinergic motor neurons, is translocated into the neuron and blocks the release of acetylcholine.

*Botulinum* toxins have been used in clinical settings for the treatment of neuromuscular disorders characterized by hyperactive skeletal muscles. BoNt/A has been approved by the U.S. Food and Drug Administration for the treatment of blepharospasm, strabismus and hemifacial spasm. Non-serotype A *botulinum* toxin serotypes apparently have a lower potency and/or a shorter duration of activity as compared to BoNt/A. Clinical effects of intramuscular of a *botulinum* toxin, such as BoNt/A, can be noted in a matter of hours. Thus, it is important to note that most if not all of the *botulinum* toxins can, upon intramuscular injection, produce significant muscle paralysis within one day of the injection, as measured, for example, by the mouse Digit Abduction Score (DAS). Aoki K. R., *Preclinical Update on BOTOX (Botulinum Toxin Type A)-Purified Neurotoxin Complex Relative to Other Botulinum Toxin Preparations*, Eur J. Neur 1999, 6 (suppl 4):S3-S10. The typical duration of symptomatic relief from a single intramuscular injection of BoNt/A averages about three months. *Botulinum* toxins, including, *botulinum* toxin type A, with reduced periods of in vivo biological activity are set forth in co-pending U.S. patent application Ser. No. 09/620840, which application is incorporated herein by reference in its entirety.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* serotypes A and E both cleave the 25 kiloDalton (kD) synaptosomal associated protein (SNAP-25), but they target different amino acid sequences within this protein. BoNT/B, D, F and G act on vesicle-associated protein (VAMP, also called synaptobrevin), with each serotype cleaving the protein at a different site. Finally, *botulinum* toxin serotype $C_1$ (BoNT/$C_1$) has been shown to cleave both syntaxin and SNAP-25. These differences in mechanism of action may affect the relative potency and/or duration of action of the various *botulinum* toxin serotypes.

Regardless of serotype, the molecular mechanism of toxin intoxication appears to be similar and to involve at least three steps or stages. In the first step of the process, the toxin binds with high affinity to the presynaptic membrane of the target neuron through a specific interaction between the H chain and a cell surface receptor; the receptor is thought to be different for each serotype of *botulinum* toxin and for tetanus toxin. The carboxyl end segment of the H chain, $H_c$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of *botulinum* toxin activity appears to involve cleavage of the critical intracellular exocytosis proteins by the L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin/B/D,/F, and/G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the *botulinum* toxin protein molecule, for all seven of the known *botulinum* toxin serotypes, is about 150 kD. Interestingly, the *botulinum* toxins are released by *Clostridial* bacterium as complexes comprising the 150 kD *botulinum* toxin protein molecule along with associated non-toxin proteins. Thus, the BoNt/A complex can be produced by *Clostridial* bacterium as 900 kD, 500 kD and 300 kD forms. BoNT/B and $C_1$ are apparently produced as only a 500 kD complex. BoNT/D is produced as both 300 kD and 500 kD complexes. Finally, BoNT/E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

BoNt/A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the BoNt/B serotype only cleave a portion of the toxin produced. The exact proportion of nicked to unnicked molecules depends on the length of incubation and the temperature of the culture. Therefore, a certain percentage of any preparation of, for example, the BoNt/B toxin is likely to be inactive, possibly accounting for the known significantly lower potency of BoNt/B as compared to BoNt/A. The presence of inactive *botulinum* toxin molecules in a clinical preparation will contribute to the overall protein load of the preparation, which has been linked to increased antigenicity, without contributing to its clinical efficacy. Additionally, it is known that BoNt/B has, upon intramuscular injection, a shorter duration of activity and is also less potent than BoNt/A at the same dose level.

It has been reported that BoNt/A has been used in clinical settings as follows:
(1) about 75-125 units of BOTOX®[1] per intramuscular injection (multiple muscles) to treat cervical dystonia;
(2) 5-10 units of BOTOX® per intramuscular injection to treat glabellar lines (brow furrows) (5 units injected intramuscularly into the procerus muscle and 10 units injected intramuscularly into each corrugator supercilii muscle);
(3) about 30-80 units of BOTOX® to treat constipation by intrasphincter injection of the puborectalis muscle;
(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).
(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

[1] Available from Allergan, Inc., of Irvinve, Calif. under the tradename BOTOX®.

The success of BoNt/A to treat a variety of clinical conditions has led to interest in other *botulinum* toxin serotypes. A study of two commercially available BoNT/A preparations (BOTOX® and Dysport®) and preparations of BoNT/B and F (both obtained from Wako Chemicals, Japan) has been carried out to determine the preclinical local muscle weakening efficacy, safety and antigenic potential. *Botulinum* toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or BoNt/B (50.0 to 400.0 units/kg), and were tested for muscle weakness and increased water consumption, the later being a putative model for dry mouth. Antigenic potential was assessed by monthly intramuscular injections in rabbits (2.0 or 8.7 Units/kg for BoNt/B or 3.0 Units/kg for BOTOX®). Peak muscle weakness and duration were dose related for all serotypes. DAS $ED_{50}$ values (units/kg) were as follows: BOTOX®: 6.7, Dysport®: 24.7, BoNt/B: 11.8 to 244.0, BoNT/F: 4.3. BOTOX® had a longer duration of action than BoNt/B or BoNt/F. Therapeutic index values were as follows: BOTOX®: 10.5, Dysport®: 6.3, BoNt/B: 4.8. Water consumption was greater in mice injected with BoNt/B than with BOTOX®, although BoNt/B was less effective at weakening muscles. After four months of injections 2 of 4 (where treated with 1.5 ng/kg) and 4 of 4 (where treated with 6.5 ng/kg) rabbits developed antibodies against BoNt/B. In a separate study, 0 of 9 BOTOX® treated rabbits demonstrated antibodies against BoNt/A. DAS results indicate relative peak potencies of BoNt/A being equal to BoNt/F, and BoNt/F being greater than BoNt/B. With regard to duration of effect, BoNt/A was greater than BoNt/B, and BoNt/B duration of effect was greater than BoNt/F. As shown by the therapeutic index values, the two commercial preparations of BoNt/A (BOTOX® and Dysport®) are different. The increased water consumption behavior observed following hind limb injection of BoNt/B indicates that clinically significant amounts of this serotype entered the murine systemic circulation. The results also indicate that in order to achieve efficacy comparable to BoNt/A, it is necessary to increase doses of the other serotypes examined. Increased dosage can comprise safety. Furthermore, in rabbits, serotype B was more antigenic than was BOTOX®, possibly because of the higher protein load injected to achieve an effective dose of BoNt/B.

The tetanus neurotoxin acts mainly in the central nervous system, while *botulinum* neurotoxin acts at the neuromuscular junction; both act by inhibiting acetylcholine release from the axon of the affected neuron into the synapse, resulting in paralysis. The effect of intoxication on the affected neuron is long-lasting and until recently has been thought to be irreversible. The tetanus neurotoxin is known to exist in one immunologically distinct serotype.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system release the neurotransmitter norepinephrine. In most instances acetylcholine has an excitatory effect. However, acetylcholine is known to have inhibitory effects at some of the peripheral parasympathetic nerve endings, such as inhibition of the heart by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the. intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

As discussed above, the present methods of treating injured muscles are still inadequate. There is a need to have improved methods of treating injured muscles.

SUMMARY

In accordance with the present invention, an effective method for treating an injured muscle includes the step of in vivo, local administration of a therapeutically effective amount of a neurotoxin into or to the vicinity of the injured muscle. The neurotoxin functions to provide a temporary chemodenervation of the injured muscle and to reduce the muscle's contractions. An objective of the present invention is therapy is to facility healing and a speedy return to function of an injured muscle. The injured muscle may be, for example, a strained muscle. In one embodiment, the neurotoxin is administered intramuscularly or subcutaneously. In another embodiment, the step of administering a neurotoxin is preceded by and/or followed by physical therapy and/or surgery.

Further in accordance with the invention, the step of administering the neurotoxin is immediately after the muscle is injured, or is as soon thereafter as is practical. In one embodiment, the neurotoxin is effective to immobilize or to substantially immobilize the injured muscle during at least phase 1 and/or phase 2 of the repair process of the injured muscle.

In accordance with the invention, the neurotoxin can include a targeting component, a therapeutic component and a translocation component. The targeting component can bind to a presynaptic motor neuron. In one embodiment, the targeting component can comprise a carboxyl end fragment of a heavy chain of a *butyricum* toxin, a *tetani* toxin, or of a *botulinum* toxin type A, B, $C_1$, D, E, F, G or a variant thereof. The therapeutic component can interfere with or modulate the release of a neurotransmitter from a neuron or its processes. In one embodiment, the therapeutic component comprises a light chain of a *butyricum* toxin, a *tetani* toxin, or of a *botulinum* toxin type A, B, $C_1$, D, E, F, G or a variant thereof. The translocation component can facilitate the transfer of at least a part of the neurotoxin, for example the therapeutic component, into the cytoplasm of the target cell. In one embodiment, the translocation component can comprise an amino end fragment of a heavy chain of a *butyricum* toxin, a *tetani* toxin, or of a *botulinum* toxin type A, B, $C_1$, D, E, F, G or variants thereof.

Still further in accordance with the invention, the neurotoxin is a *botulinum* toxin type A, B, E and/or F. In a preferred embodiment, the neurotoxin used to treat an injured muscle is *botulinum* toxin type A. In fact, the use of *botulinum* toxin type A is preferred because of its commercial availability, known clinical uses, and successful application to treat muscle injury according to the present invention, as disclosed herein. Use of from about 0.1 U/kg to about 30 U/kg of a *botulinum* toxin type A and from about 1 U/kg to about 150 U/kg of a *botulinum* toxin type B is within the scope of a method practiced according to the present disclosed invention. With regard to the other *botulinum* toxin serotypes (including toxin types E and F) the U/kg dosage to be used is within the range of about 0.1 U/kg to about 150 U/kg, as set forth herein.

Still further in accordance with the invention, the neurotoxin can be recombinantly produced.

A detailed embodiment of the present invention is a method for treating (as by promoting the healing of) an injured muscle by in vivo, local administration of a therapeutically effective amount of a *botulinum* toxin to an injured muscle, thereby treating the injured muscle. The *botulinum* toxin can be *botulinum* toxin type A. Significantly, the present invention also encompasses a method for treating pain associated with an injured muscle by in vivo, local administration of a therapeutically effective amount of a *botulinum* toxin to an injured muscle, thereby reducing the pain associated with an injured muscle.

Each and every feature described herein, and each and every combination of two or more of such features, is included within the scope of the present invention provided that the features included in such a combination are not mutually inconsistent.

Definitions

The following definitions are provided and apply herein.

"About" means approximately or nearly and in the context of a numerical value or range set forth herein means ±10% of the numerical value or range recited or claimed.

"Heavy chain" means the heavy chain of a *clostridial* neurotoxin. It preferably has a molecular weight of about 100 kDa and may be referred to herein as H chain or as H. "$H_N$" means a fragment (preferably having a molecular weight of about 50 kDa) derived from the H chain of a *Clostridial* neurotoxin which is approximately equivalent to the amino terminal segment of the H chain, or the portion corresponding to that fragment in the intact in the H chain. It is believed to contain the portion of the natural or wild type *clostridial* neurotoxin involved in the translocation of the L chain across an intracellular endosomal membrane. "$H_c$" means a fragment (about 50 kDa) derived from the H chain of a *clostridial* neurotoxin which is approximately equivalent to the carboxyl terminal segment of the H chain, or the portion corresponding to that fragment in the intact H chain. It is believed to be immunogenic and to contain the portion of the natural or wild type *Clostridial* neurotoxin involved in high affinity, presynaptic binding to motor neurons.

"Injured muscle" includes a strained, torn or pulled muscle, as well as a muscle with a contusion (bruise), laceration, ischemia or rupture.

"Light chain" means the light chain of a *clostridial* neurotoxin. It preferably has a molecular weight of about 50 kDa, and can be referred to as L chain, L or as the proteolytic domain (amino acid sequence) of a *clostridial* neurotoxin. The light chain is believed to be effective as an inhibitor of neurotransmitter release when it is released into a cytoplasm of a target cell.

"Local administration" means direct administration of a pharmaceutical at or to the vicinity of a site on or within an animal body, at which site a biological effect of the pharmaceutical is desired. Local administration excludes systemic routes of administration, such as intravenous or oral administration.

"Neurotoxin" means a chemical entity that is capable of interfering with or modulating at least one function of a neuron. The "neurotoxin" can be naturally occurring or man-made. Furthermore, the "neurotoxin" can be a small molecule, a large molecule, a polypeptide, a conjugated-polypeptide or mixtures thereof.

"Variant" means a chemical entity which is slightly different from a parent chemical entity but which still has a biological effect. The biological effect of the variant may be substantially the same or better than that of the parent. For example, a variant light chain of a *botulinum* toxin having at least one amino acid replaced, modified, deleted or added, may have the same or better ability to prevent the release of neurotransmitter vesicles. Additionally, the biological effect of a variant may be decreased. For example, a variant light chain of a *botulinum* toxin type A having a leucine-based motif removed may have a shorter biological persistence than that of the parent (or native) *botulinum* toxin type A light chain.

DESCRIPTION

In a broad embodiment, an effective method for treating an injured muscle according to the present invention can include the step of locally administering a therapeutically effective amount of a neurotoxin into an injured muscle. Preferably, the injured muscle is a strained muscle.

A strain injury of the skeletal muscle may be classified as a shearing injury. In shearing injury, not only the myofibers but also the mysial sheaths are torn. Almost immediately after the injury of the muscle, a repair process of muscle begins. The repair process of the shearing injury may be divided into three phases.

Phase 1 is the destruction phase, which is characterized by hematoma formation, myofiber necrosis, and inflammatory cell reaction. The site of rupture of an otherwise healthy muscle often occurs close to its distal myotendinous junction (MTJ) after a strain. The ruptured myofibers contract and a gap is formed between the stumps. Because skeletal muscle is richly vascularized, hemorrhage from the torn vessels is inescapable and the gap becomes filled with a hematoma, later replaced by scar tissue. In shearing injuries the mechanical force tears the entire myofiber, damaging the myofiber plasma membrane and leaving sarcoplasm open at the ends of the stumps. Because myofibers are very long, string-like cells, the necrosis initiated at this site extends all along the whole length of the ruptured myofiber. The blood vessels are also torn in shearing injuries; thus, blood-borne inflammatory cells gain immediate access to the injury site to induce an inflammation. Phase 1 persists for about 2 to 3 days following the injury.

Phase 2 is the repair phase, which consists of phagocycosis of the necrotized tissue, regeneration of the myofibers, production of connective tissue scar, and capillary ingrowth. The key step in the regeneration of injured muscle tissue is the vascularization of the injured area. The restoration of vascular supply is a necessary for the regeneration of an injured muscle. The new capillaries sprout from surviving trunks of blood vessels and pierce coward the center of injured area. These new capillaries help provide adequate oxygen supply to the regenerating area.

Phase 3 is the remodeling phase, which consists of maturation of the regenerated myofibers, contraction and reorganization of the scar tissue, and restoration of the functional capacity of the repaired muscle. Phase 2 (repair) and 3 (remodeling) often occur simultaneously and persists for about 2 days to about six weeks following phase 1.

In one embodiment of the present invention, the neurotoxin is locally administered, preferably intramuscularly, to immobilize the injured muscle to facilitate healing. Local administration of a neurotoxin according to the present disclosed invention can also reduce the pain experienced due to a muscle injury. Preferably, the administration of the neurotoxin is immediately at the time of injury or closely thereafter. In one preferred embodiment, the neurotoxin is effective to immobilize the injured muscle during the destruction phase (phase 1) to prevent re-rupturing of the muscle.

Without wishing to limit the invention to any particular theory of mechanism of operation, it is believed that mobilization during the repair and/or remodeling phases is beneficial in that such mobilization induces more rapid and intensive capillary ingrowth to the injured area, as well as better muscle fiber regeneration and orientation. Therefore, in one embodiment, the immobilizing effect of the neurotoxin is absent during the repair phase (phase 2) and/or remodeling phase (phase 3). In a more preferred embodiment, the neurotoxin is administered and is effective to immobilize the injured muscle during phase 1, but not during phases 2 and 3 of the repair process. For example, if the neurotoxin is injected, preferably intramuscularly, immediately to the muscle following an injury, it is preferable that the neurotoxin immobilizes the injured muscle for about 3 days after the time of administration. Alternatively, the neurotoxin can have its immobilization effect only up to the point where the patient experiences little or no pain in the use of the injured muscle in basic movements. When this critical point is reached, the patient should be encouraged to start active, progressive mobilization.

In another embodiment of the present invention, the neurotoxin is effective to immobilize the injured muscle for all of the phase 1-3 periods and for a subsequent muscle injury recovery period thereafter.

Neurotoxins, such as certain of the *botulinum* toxins, which can require from less than about one day to about seven days to exhibit significant clinical muscle paralysis effect and/or and where the muscle paralysis effect is sustained post injection for a period of several months, are within the scope of the present invention, as such neurotoxins can be used to treat relatively serious or long lasting muscle injuries or where a long period of muscle immobilization is indicated for proper healing.

In a broad embodiment, the neurotoxin is a neuromuscular blocking agent. Table 1 shows a non-limiting list of neuromuscular blocking agents and their potential site of actions. In an embodiment, neuromuscular blocking agents having the ability to immobilize muscles, preferably injured muscles, for at least about 5 days, and preferably for at least about 3 days are administered to treat injured muscles. In a preferred embodiment of the present invention, the neurotoxin is a *botulinum* toxin because of the known uses and clinical safety of a *botulinum* toxin, such as *botulinum* toxin type E to treat muscle disorders, such as muscle spasms. In a particularly preferred embodiment of the present invention, especially for severe, or third degree muscle injuries, the locally administered *botulinum* toxin is a *botulinum* toxin type E. *Botulinum* toxin type A can also be used in both these embodiments.

TABLE 1

| Compound | Site of Action Relative to NMJ | Pharmacological Class |
|---|---|---|
| Acetylcholine Esterase Inducers | Synaptic | ACh Esterase Inducers |
| Aconitine | Presynaptic | Sodium Channel Activator |
| Adenoregulin (from the frog *Phyllomedeusa bicolor*) | Presynaptic | Adenosine Receptor Regulator |
| Adenosine Agonist | Pre & Post Synaptic | Adenosine |
| Adenosine Antagonist | Pre & Post Synaptic | Adenosine |
| Adenosine | Pre & Post Synaptic | Adenosine |
| Regulating Agent | | |
| Adrenergics | Presynaptic | Alpha Adrenergic |
| Anatoxin-A | Postsynaptic | AChR Agonist |
| Antiepileptics | CNS | Antiepileptics |
| Antisense | Pre & Post Synaptic | Antisense technology for specific proteins or messages important in neurotransmitter release, receptor production. |
| Anxiolytics | CNS | Anxiolytics Antiepileptic |
| Atacurium | Postsynaptic | AChR Antagonist Nondepolarizing muscle relaxant |
| Atracurium besylate (Tracurium) | Postsynaptic | AChR Antagonist Nondepolarizing muscle relaxant |
| Baclofen (Lioresal .RTM., Geigy; Intrathecal, Medtronic Neurological; generic, Athena, Biocraft, Warner Chilcott) | Presynaptic | GABA analog |
| Bacterial, Plant and Fungal Products | | |
| Batrachotoxin | Presynaptic | Sodium Channel Activator |
| Benzylpiperidines | Synaptic Cleft | ACh Esterase Inhibitors (nontraditional) |
| Botanical Neurotoxins | Pre and Post Synaptic as well as Synaptic Cleft | varies |
| Bungarotoxin-β (β-BuTX) | Presynaptic | PLA2 and voltage sensitive potassium channel blocker. Snake toxin from *Bungarus multicinctus*. |
| Bupivacain | Pre and Post Synaptic | Local Anesthetic Myotoxin |

TABLE 1-continued

| Compound | Site of Action Relative to NMJ | Pharmacological Class |
|---|---|---|
| Captopril(Capoten .RTM., Squibb; Capzide .RTM., Squibb) | Presynaptic | Antihypertensive ACE Inhibitor zinc endopeptidase inhibitor |
| Choline+ acetyl transferase inhibitors | Pre Synaptic | CAT Inhibitors |
| Cholinesterase Inhibitors | Synaptic Cleft | ACh Esterase Inhibitors |
| Ciguatoxins | Presynaptic | Sodium Channel |
| Conotoxin MI (alpha Conotoxin) | Postsynaptic | AChR Antagonist |
| Conotoxin-.mu. GIIIA (mu-CT) | | Na+ channel blocker |
| Conotoxin-.OMEGA. GVIA (omega-CT) | | Ca2+ channel blocker in neutrons only |
| Curare | Postsynaptic | AChR Antagonist Nondepolarizing |
| Dantrolene Sodium (Dantrium, P & G) | Postsynaptic | Skeletal Muscle Relaxant |
| Dauricine | Post Synaptic | AChR antagonist |
| Decamethonium Bromide | Presynaptic | Ganglionic blocker |
| Dendrotoxin | Pre and Post Synaptic | Potassium Channel blocker |
| Diaminopyridine (3-DAP) | Presynaptic | Botulinum toxin intoxication Reversal |
| Diazepam | CNS | Anxiolytic |
| Doxacurium chloride (Nuromax .RTM., Burroughs Wellcome) | Postsynaptic | AChR Antagonist Nondepolarizing muscle relaxant |
| Doxorubicin (Adriamyocin, Adria; Rubex, Immunex; Cetus Oncology) | Postsynaptic | Myotoxin Chemo Myectomy |
| Epibatidine Dihydrochloride | Postsynaptic | AChR Agonist |
| Felbamate (Felbatol, Carter-Wallace lic to Schering-Plough) | Presynaptic CNS | Antiepileptic |
| Foroxymithine | Presynaptic | Angiotensin I Converting Enzyme inhibitor |
| Gabapentin (Neurontin, Parke-Davis) | Presynaptic CNS | Antiepileptic GABA Analog |
| Gallamine | Postsynaptic | AChR Antagonist |
| Grayantoxin | Presynaptic | Sodium Channel Activator |
| Hexahydroazepinyl Acetamides and other chemical classes | Presynaptic | ACh Releaser |
| Huperzine A | Synaptic Cleft | ACh Esterase Inhibitor |
| Insect Venoms | | |
| Ion Channel Blockers | Pre and Post Synaptic | Channel Blockers |
| Ion Channel Stimulants | Pre and Post Synaptic | Channel Stimulants |
| Latrotoxin-α | Presynaptic | Calcium Ionophore black widow spider venom component |
| Lidocaine, procaine, mepivacain, etc. | Presynaptic | Local Anesthetics |
| Linopirdine (DuP 996, Dupont Merck) | Presynaptic | ACh Release Enhancer |
| Lophotoxin and analogs | Postsynaptic | AChR Antagonist Irreversible |
| Marine Natural Products | | |
| Methocarbamol (Robaxin, Robins Co.) | | CNS Depression, muscle relaxation. |

TABLE 1-continued

| Compound | Site of Action Relative to NMJ | Pharmacological Class |
|---|---|---|
| Methyllycaconitine Mivacurium chloride (Mivacro .RTM., BW-BW1090U, Burroughs Wellcome) | Postsynaptic | AChR Antagonist Nondepolarizing muscle relaxant |
| Modified Clostridial Toxins Monoclonal antibodies against NMJ components | Pre Synaptic | ACh Release Inhibitor receptor, agrin, neurotransmitters, plasma membrane components, inactivating enzymes, etc. |
| Muscarinic Agonist and Antagonists | Pre and Post Synaptic, | Muscarinic CNS Agonist Antagonist |
| Neosaxitoxin Neosurugatoxin | Presynaptic | Sodium Channel Blocker Autonomic Ganglionic AChR Blocker. (no effect @ NMJ) |
| Neuromuscular Blocking Agents | Postsynaptic | AChR Antagonists AChR Depolarizing |
| Neurotoxins from reptile, insects, and other sources | Pre and Post Synaptic as well as Synaptic Cleft | varies |
| Pancuronium Bromide (Organon) | Postsynaptic | AChR Antagonist Nondepolarizing muscle relaxant |
| Pancuronium-3-OH metabolites (Organon) | Postsynaptic | AChR Antagonist Nondepolarizing muscle relaxant |
| Papverine HCl (30 mg/ml) | | Smooth Muscle Relaxants |
| Physostigmine and Analogs | Synaptic Cleft | ACh Esterase inhibitor |
| Pipercuronium (Arduan, Organon) | Postsynaptic | AChR Antagonist Nondepolarizing muscle relaxant |
| Presynaptic Nerve Terminal Recpetors | Pre Synaptic | any extra or intraneuronal recpetors on nerve terminal |
| Short Neurotoxin alpha β-Bungarotoxin (β-BuTX) | Postsynaptic Presynaptic | AChR Antagonist Snake toxin from *Bungarus multicinctus*. |
| Succinylcholine chloride (Anectine, Burroughs Wellcome) | Postsynaptic | AChR Receptor Agonist Depolarizing skeletal muscle relaxant |
| Tetanus Toxin Tetanus Toxin Transporter | Presynaptic Presynaptic Synaptic | EAA release inhibitor ACh Esterase Inhibitor |
| Tetrahydroamino-acridine (THA) | Cleft | |
| Tetrodoxtoxin | Pre and Post Synaptic | Sodium Channel Blocker |
| Tiagabine (Novo Nordisk) | CNS | Antiepileptic GABA uptake inhibitor |
| Transglutaminase inhibitors or induction prevention | Pre and Post Synaptic | Enzyme |
| Valium | | diazepam CNS Anxiolytic |
| Vecuronium (Norcuron, Organon) | Postsynaptic | AChR Antagonist Nondepolarizing muscle relaxant |
| Vecuronium-3-OH metabolites (Organon) | Postsynaptic | AChR Antagonist Nondepolarizing muscle relaxant |
| Veratridine | Presynaptic | Sodium Channel Activator |
| Vigabatrin (Sabril, Marion Merrell Dow) | Presynaptic CNS | Antiepileptic GABA metabolism inhibitor (irreversible) |
| Vesamicol and other drugs with the same mechanism. | Presynaptic | ACh Vesicle transport inhibitor |
| Zinc Endopeptidase and other proteases delivered by Botulinum toxin or tetanus toxin transporter | Pre Synaptic | Enyzmes. reduce neurotransmitter release |

In a broad embodiment, the neurotoxin can comprise a targeting component, a therapeutic component and a translocation component. The targeting component can bind to a presynaptic motor neuron. In one embodiment, the targeting component can comprise a carboxyl end fragment of a heavy chain of a *butyricum* toxin, a *tetani* toxin, a *botulinum* toxin type A, B, C1, D, E, F, G or a variant thereof. In a preferred embodiment, the targeting component can include a carboxyl end fragment of a *botulinum* toxin type A.

The therapeutic component can substantially interfere with or modulate the release of neurotransmitters from a cell or its processes. In one embodiment, the therapeutic component comprises a light chain of a *butyricum* toxin, a *tetani* toxin, a *botulinum* toxin type A, B, $C_1$, D, E, F, G or a variant thereof. In a preferred embodiment, the therapeutic component may include a light chain of a *botulinum* toxin type which has a short biological persistence, for example less than about 5 days, preferably less than about 3 days. Preferably, such light chain can be a light chain of a *botulinum* toxin type E or F. Alternately, the light chain can be a light chain of a *botulinum* toxin type A.

The translocation component can facilitate the transfer of at least a part of the neurotoxin, for example the therapeutic component into the cytoplasm of the target cell. In one embodiment, the translocation component comprises an amino end fragment of a heavy chain of a *butyricum* toxin, a *tetani* toxin, a *botulinum* toxin type A, B, $C_1$, D, E, F, G or variants thereof. In a preferred embodiment, the translocation component comprises an amino end fragment of a heavy chain of a *botulinum* toxin type A.

In one embodiment, the targeting component comprises a carboxyl end fragment of a heavy chain of a *botulinum* toxin type E or F, the therapeutic component comprises a light chain of a *botulinum* toxin type E or F and the translocation component comprises an amine end fragment of a heavy chain of a *botulinum* toxin type E or F. In a preferred embodiment, the neurotoxin comprises a *botulinum* toxin type E. In another preferred embodiment, the neurotoxin comprises a *botulinum* toxin type F. In yet another embodiment, the neurotoxin comprises a mixture of *botulinum* toxin type E and F.

In one embodiment, the targeting component comprises a carboxyl end fragment of a heavy chain of a *botulinum* toxin type A, the therapeutic component comprises a light chain of a *botulinum* toxin type A and the translocation component comprises an amine end fragment of a heavy chain of a *botulinum* toxin type A. In a preferred embodiment, the neurotoxin of the present invention comprises a *botulinum* toxin type A. A suitable *botulinum* toxin type A to use herein is BOTOX® (Allergan, Inc., Irvine, Calif.)

Although the neurotoxins of the present invention treats injured muscles by immobilizing them, in one embodiment, the neurotoxin may also be administered to injured muscles to reduce pain and/or spasm. In another embodiment, the neurotoxin is able to immobilize the injured muscle and to reduce pain associated with that injured muscle. In a preferred embodiment, a neurotoxin, for example a *botulinum* toxin type E, pr most preferably type A, is administered to a strained muscle to immobilize the muscle and/or to reduce pain associated with that muscle.

Of course, an ordinarily skilled medical provider can determine the appropriate dose and frequency of administration(s) to achieve an optimum clinical result. That is, one of ordinary skill in medicine would be able to administer the appropriate amount of the neuromuscular blocking agent at the appropriate time(s) to effectively immobilize the injured muscle(s). The dose of the neurotoxin to be administered depends upon a variety of factors, including the size of the muscle, the severity of the muscle injury. In a preferred embodiment, the dose of the neurotoxin administered immobilizes the injured muscle(s) for no longer than the duration of phase 1 of the repair process. In the various methods of the present invention, from about 0.1 U/kg to about 15 U/kg, of *botulinum* toxin type A can be administered to the injured muscle. Preferably, about 1 U/kg to about 20 U/kg of *botulinum* toxin type A may be administered to the injured muscle. Use of from about 0.1 U/kg to about 30 U/kg of a *botulinum* toxin type A and from about 1 U/kg to about 150 U/kg of a *botulinum* toxin type B is within the scope of a method practiced according to the present disclosed invention. With regard to the other *botulinum* toxin serotypes (including toxin types E and F) the U/kg dosage to be used is within the range of about 0.1 U/kg to about 150 U/kg, as set forth herein.

Although intramuscular injection is the preferred route of administration, other routes of local administration are available, such as subcutaneous administration.

In another broad embodiment, the method of treating injured muscle according to this invention further includes other steps described below. These other steps may be taken prior to, in conjunction with or following the step of administering a neurotoxin, preferably to the injured muscle. For example, the present recommended treatment for strained muscle includes resting, icing, compression and elevating. These four steps (or procedures) have the same objective. They minimize bleeding from ruptured blood vessels to rupture site. This will prevent the formation of a large hematoma, which has a direct impact on the size of scar tissue at the end of the regeneration. A small hematoma and the limitation of interstitial edema accumulation on the rupture site also shorten the ischemic period in the granulation tissue, which in turn accelerates regeneration.

Other additional steps may be employed in the treatment of injured muscles. In one embodiment, the additional step include an administration of nonsteroidal anti-inflammatory drugs (NSAIDs), therapeutic ultrasound, hyperbaric oxygen, and in severe injuries, surgery may also be employed. NSAIDs should be a part of early treatment and should he started immediately after the injury. Short-term use of NSAIDs in the early phase of healing decreases the inflammatory cell reaction, and has no adverse effects on tensile or contractile properties of injured muscle.

In another embodiment, the additional step includes the use of therapeutic ultrasound. Therapeutic ultrasound is widely recommended and used in the treatment of muscle strains. It is thought that therapeutic ultrasound promotes the proliferation phase of myoregeneration.

In another embodiment, the additional step includes the use of hyperbaric oxygen. It is known that hyperbaric oxygen therapy in rabbits during the early phase of the repair substantially improves the final outcome. It is believed that such hyperbaric oxygen therapy in other mammals, for example human beings, may be helpful, such as by speeding up muscle regeneration.

In another embodiment, the additional step includes surgical intervention. Surgical treatment of muscle injuries should be reserved for the most serious injuries, because in most cases conservative treatment results in a good outcome. Surgical treatment is indicated only in cases of (1) large-intramuscular hematomas, (2) third-degree strains or tears of muscles with few or no agonise muscles, and (3) second-degree strains, if more than half of the muscle belly is torn.

In another broad aspect of this invention, recombinant techniques are used to produce at least one of the components of the neurotoxins. The technique includes steps of obtaining genetic materials from either DNA cloned from natural sources, or synthetic oligonucleotide sequences, which have codes for one of the components, for example the therapeutic, translocation and/or targeting component(s). The genetic constructs are incorporated into host cells for amplification by first fusing the genetic constructs with a cloning vectors, such as phages or plasmids. Then the cloning vectors are inserted into hosts, preferably *E. coli's*. Following the expressions of the recombinant genes in host cells, the resultant proteins can be isolated using conventional techniques. The protein expressed may comprise all three components of the neurotoxin. For example, the protein expressed may include a light chain of *botulinum* toxin type E (the therapeutic component), a heavy chain, preferably the $H_N$, of a *botulinum* toxin type B (the translocation component), and an $H_c$ of *botulinum* toxin type A, which selectively binds to the motor neurons. In one embodiment, the protein expressed may include less than all three components of the neurotoxin. In such case, the components may be chemically joined using techniques known in the art.

There can be many advantages to producing these neurotoxins recombinantly. For example, production of neurotoxin from anaerobic *Clostridium* cultures is a cumbersome and time-consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL-3). During the fermentation process, the folded single-chain neurotoxins are activated by endogenous *Clostridial* proteases through a process termed nicking. This involves the removal of approximately 10 amino acid residues from the single-chain to create the dichain form in which the two chains remain covalently linked through the intrachain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the type and amounts of proteolytic activity produced by a given strain. For example, greater than 99% of *Clostridial botulinum* type A single-chain neurotoxin is activated by the Hall A *Clostridial botulinum* strain, whereas type B and E strains produce toxins with lower amounts of activation (0 to 75% depending upon the fermentation time). Thus, the high toxicity of the mature neurotoxin plays a major part in the commercial manufacture of neurotoxins as therapeutic neurotoxins.

The degree of activation of engineered *Clostridial* toxins is, therefore, an important consideration for manufacture of these materials. It would be a major advantage if neurotoxins such as *botulinum* toxin and tetanus toxin could be expressed, recombinantly, in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in *E. coli* and purification of individual H and L chains of tetanus and *botulinum* toxins; these isolated chains are, by themselves, non-toxic; see Li et al., *Biochemistry* 33:7014-7020 (1994); Zhou et al., *Biochemistry* 34:15175-15181 (1995), hereby incorporated by reference herein. Following the separate production of these peptide chains and under strictly controlled conditions the H and L subunits can be combined by oxidative disulphide linkage to form the neuroparalytic di-chains.

The following non-limiting examples provide preferred methods of treating injured muscles and producing recombinant neurotoxins, preferably *botulinum* toxins. The methods of producing recombinant *botulinum* toxins described in the below Examples 4-8 are drawn from and are similar to those described in Dolly et al. International Patent Application No. WO 95/32738, the disclosure of which is incorporated in its entirety herein by reference.

EXAMPLE 1

Treatment of a Ruptured Biceps Tendon

Ruptures of the biceps brachii commonly occur at the proximal end and involve the long head of the biceps. The muscle may rupture at the distal insertion onto the radius, but is rare. Most often, ruptures occur in adults older than age 40 years who have a long history of shoulder pain secondary to an impingement syndrome. Over time, the tendon becomes frayed and weak, and ultimately ruptures, partially or entirely. Regardless, the rupture is often caused by a trivial event. These ruptures are usually associated with a rotator cuff tear, especially among the elderly.

A 45 year old man presents with a bulge in the lower arm after lifting heavy boxes. He reports a history of sudden sharp pain in the upper arm, often accompanied by an audible snap. The man is diagnosed as having a ruptured biceps tendon and is at the beginning of phase 1 of the repair process. The rupture may be classified as a mild second degree strain.

The patient is treated by a bolus injection of between about 0.1 U/kg to about 25 U/kg of a neurotoxin intramuscularly to the biceps. Preferably the neurotoxin is *botulinum* toxin type E and/or F, more preferably type A. The particular dose and frequency of administrations depend upon a variety of factors, and are to be determined by the treating physician. The patient is further instructed to rest and apply ice and compression to the biceps. Within about three days after the administration of the neurotoxin, the patient is able to bend his arm. Also, after about three days, the patient experiences a reduction in inflammation, which is a sign that the patient is entering into phase 2 and 3 of the repair process. The patient also experiences a significant pain reduction. Local administration of from about 10 units to about 200 units of *botulinum* toxin type A can also be used for long term (2-4 months) muscle immobilization and pain reduction.

EXAMPLE 2

Extensor Mechanism Rupture

Rupture of the extensor mechanism of the knee occurs in one of two ways: in younger patients as a result of a sudden or violent force (such as jumping, heavy lifting); and in older patients as a result of relatively trivial force. In either group, there may have been some prior arching. This condition affects older patients who have typically been somewhat sedentary and have suddenly increased their activity level, or patient who have had some preexisting or co-existing condition such as diabetes mellitus, rheumatoid arthritis, and other systemic inflammatory disorders, or prior knee surgery.

A 22 year old female soccer player presents with an inability to extend her knee. The patient also is also unable to do straight leg raise, but is able to walk if she keeps a hand on her thigh and maintain her knee in extension. A plain radiograph shows that the patella is in a lower than usual location. The patient is diagnosed with a severe rupture of the quadriceps.

After determining the injury is severe (third degree), the patient agrees to undergo reparative surgery. Post-operationally, the patient is treated by a bolus injection of between about 0.1 U/kg to about 25 U/kg of a neurotoxin (such as about 10 units to about 400 units of *botulinum* toxin type A) intramuscularly to the quadriceps. Preferably the neurotoxin is *botulinum* toxin type A. The particular dose and frequency of administrations depend upon a variety of factors, and are to be determined by the treating physician. The patient is further instructed to rest and apply ice and compression to the quadriceps. Within about 15 days after the administration of the neurotoxin, gradual movement and activity of the injured muscle is possible. The patient is then encouraged to gently move the recovering muscle to strengthen it and the surrounding muscles. As the toxin effect wears off some more, the patient would then have the ability to rapidly participate in a physical therapy program or resume the general activity and/or sport. If this patient depended upon this sport for her livelihood, *botulinum* toxin therapy would facilitate her early return to this activity. Local administration of from about 10 units to about 200 units of *botulinum* toxin type A can be used for long term (2-4 months) muscle immobilization.

EXAMPLE 3

Treatment of Shin Splints

Runners commonly experience shin splits in the lower limb which causes pain and restricts this activity. The lower leg pain resulting from shin splits is caused by very small tears in the leg muscles at their point of attachment to the shin. There are two types: 1. Anterior shin splints occur in the front portion of the shinbone (tibia). 2. Posterior shin splints occur on the inside (medial) part of the leg along the tibia.

Anterior shin splints are due to muscle imbalances, insufficient shock absorption or toe running. Excessive pronation contributes to both anterior and posterior shin splints.

In treating strained muscle, such as a shin splint, five steps are recommended: (1) Protect the injured muscle from further injury by using splints, pads and/or crutches; (2) Restrict activity, usually for 48 to 72 hours to allow the healing process to begin. The administration of a short acting *botulinum* toxin type E or F or a *botulinum* toxin type A modified so as to reduce the period of in vivo biological activity (i.e. a shorter period of flaccid muscle paralysis) of the type A toxin. Suitable *botulinum* toxins, including *botulinum* toxin type A, with reduced periods of in vivo biological activity suitable for use herein are set forth in co-pending U.S. patent application Ser. No. 09/620840, which application is incorporated herein by reference in its entirety. In more severe strains restriction of activity can last for weeks to months. With a longer required restriction of activity, an administration of a longer acting *botulinum* toxin, for example (unmodified) *botulinum* toxin type B, or more preferably, type A toxin, can be appropriate. Without this treatment, patients could experience weeks of restricted activity. As the healing process begins, gentle motion and movement of the affected muscle is advised; (3) Ice should be applied for 15-20 minutes every hour; (4) Compression such as elastic bandage should be kept-on between icing; and (5) Elevate the injured area to minimize swelling.

EXAMPLE 4

Subcloning the BoNT/A-L Chain Gene

This Example describes the methods to clone the polynucleotide sequence encoding the BoNT/A-L chain. The DNA sequence encoding the BoNT/A-L chain is amplified by a PCR protocol that employs synthetic oligonucleotides having the sequences, 5'-AAAGGCCTTTTGTTMTAAACAA-3' (SEQ ID#1) and 5'-GGAATTCTTACTTATTGTATC-CTTTA-3' (SEQ ID#2). Use of these primers allows the introduction of Stu I and EcoR I restriction sites into the 5' and 3' ends of the BoNT/A-L chain gene fragment, respectively. These restriction sites are subsequently used to facilitate unidirectional subcloning of the amplification products. Additionally, these primers introduce a stop codon at the C-terminus of the L chain coding sequence. Chromosomal DNA from C. botulinum (strain 63 A) serves as a template in the amplification reaction.

The PCR amplification is performed in a 100 µl volume containing 10 mM Tris-HCI (pH 8.3), 50 mM KCI, 1.5 mM $MgCl_2$, 0.2 mM of each deoxynucleotide triphosphate (dNTP), 50 pmol of each primer, 200 ng of genomic DNA and 2.5 units of Taq-polymerase (Promega). The reaction mixture is subjected to 35 cycles of denaturation (1 minute at 94° C.), annealing (2 minutes at 37° C.) and polymerization (2 minutes at 72° C.). Finally, the reaction is extended for an additional 5 minutes at 72° C.

The PCR amplification product is digested with Stu I and EcoR I, purified by agarose gel electrophoresis, and ligated into Sma I and EcoR I digested pBluescript II SK* to yield the plasmid, pSAL. Bacterial transformants harboring his plasmid are isolated by standard procedures. The identity of the cloned L chain polynucleotide is confirmed by double stranded plasmid sequencing using SEQUENASE (United States Biochemicals) according to the manufacturer's instructions. Synthetic oligonucleotide sequencing primers are prepared as necessary to achieve overlapping sequencing runs. The cloned sequence is found to be identical to the sequence disclosed by Binz, et al., in *J. Biol Chem.* 265:9153 (1990), and Thompson et al., in *Eur. J. Biochem.* 189:73 (1990).

Site-directed mutants designed to compromise the enzymatic activity of the BoNT/A-L chain can also be created.

EXAMPLE 5

Expression of the *Botulinum* Toxin Type A-L (BoNt/A-L) Chain Fusion Proteins

This Example describes the methods to verify expression of the wild-type L chains, which may serve as a therapeutic component, in bacteria harboring the pCA-L plasmids. Well isolated bacterial colonies harboring either pCAL are used to inoculate L-broth containing 100 µg/ml ampicillin and 2% (w/v) glucose, and grown overnight with shaking at 30° C. The overnight cultures are diluted 1:10 into fresh L-broth containing 100 µg/ml of ampicillin and incubated for 2 hours. Fusion protein expression is induced by addition of IPTG to a final concentration of 0.1 mM. After an additional 4 hour incubation at 30° C., bacteria are collected by centrifugation at 6,000 ×g for 10 minutes.

A small-scale SDS-PAGE analysis confirmed the presence of a 90 kDa protein band in samples derived from IPTG-induced bacteria. This $M_r$ is consistent with the predicted size of a fusion protein having MBP (~40 kDa) and BoNT/A-L chain (~50 kDa) components. Furthermore, when compared with samples isolated from control cultures, the IPTG-induced clones contained substantially larger amounts of the fusion protein.

The presence of the desired fusion proteins in IPTG-induced bacterial extracts is also confirmed by Western blotting using the polyclonal anti-L chain probe described by Cenci di Bello et al., in *Eur. J. Biochem.* 219:161 (1993).

Reactive bands on PVDF membranes (Pharmacia; Milton Keynes, UK) are visualized using an anti-rabbit immunoglobulin conjugated to horseradish peroxidase (Bio-Rad; Hemel Hempstead, UK) and the ECL detection system (Amersham, UK). Western blotting results confirmed the presence of the dominant fusion protein together with several faint bands corresponding to proteins of lower $M_r$ than the fully sized fusion protein. This observation suggested that limited degradation of the fusion protein occurred in the bacteria or during the isolation procedure. Neither the use of 1 mM nor 10 mM benzamidine (Sigma; Poole, UK) during the isolation procedure eliminated this proteolytic breakdown.

The yield of intact fusion protein isolated by the above procedure remained fully adequate for ell procedures described herein. Based on estimates from stained SDS-PAGE gels, the bacterial clones induced with IPTG yielded 5-10 mg of total MBP-wild-type or mutant L chain fusion protein per liter of culture. Thus, the method of producing BoNT/A-L chain fusion proteins disclosed herein is highly efficient, despite any limited proteolysis that did occur.

The MBP-L chain fusion proteins encoded by the pCAL and pCAL-TyrU7 expression plasmids are purified from bacteria by amylose affinity chromatography. Recombinant wild-type or mutant L chains are then separated from the sugar binding domains of the fusion proteins by site-specific cleavage with Factor $X_2$. This cleavage procedure yielded free MBP, free L chains and a small amount of uncleaved fusion protein. While the resulting L chains present in such mixtures have been shown to possess the desired activities, we have also employed an additional purification step. Accordingly, the mixture of cleavage products is applied to a second amylose affinity column that bound both the MBP and uncleaved fusion protein. Free L chains are not retained on the affinity column, and are isolated for use in experiments described below.

EXAMPLE 6

Purification of Fusion Proteins and Isolation of Recombinant BoNT/A-L Chains

This Example describes a method to produce and purify wild-type recombinant BoNT/A light chains from bacterial clones. Pellets from 1 liter cultures of bacteria expressing the wild-type BoNT/A-L chain proteins are resuspended in column buffer [10 mM Tris-HCI (pH 8.0), 200 mM NaCl, 1 mM EGTA and 1 mM DTT] containing 1 mM phenyl-methane-sulfonyl fluoride (PMSF) and 10 mM benzamidine, and lysed by sonication. The lysates are cleared by centrifugation at 15,000 ×g for 15 minutes at 4° C. Supernatants are applied to an amylose affinity column [2×10 cm, 30 ml resin] (New England BioLabs; Hitchin, UK). Unbound proteins are washed from the resin with column buffer until the eluate is free of protein as judged by a stable absorbance reading at 280 nm. The bound MBP-L chain fusion protein is subsequently eluted with column buffer containing 10 mM maltose. Fractions containing the fusion protein are pooled and dialyzed against 20 mM Tris-HCl (pH 8.0) supplemented with 150 mM NaCl, 2 mM, CaCl$_2$ and 1 mM DTT for 72 hours at 4° C.

Fusion proteins are cleaved with Factor X$_2$ (Promega; Southampton, UK) at an enzyme:substrate ratio of 1:100 while dialyzing against a buffer of 20 mM Tris-HCl (pH 8.0) supplemented with 150 mM NaCl, 2 mM, CaCl$_2$ and 1 mM DTT. Dialysis is carried out for 24 hours at 4° C. The mixture of MBP and either wild-type or mutant L chain that resulted from the cleavage step is loaded onto a 10 ml amylose column equilibrated with column buffer. Aliquots of the flow through fractions are prepared for SDS-PAGE analysis to identify samples containing the L chains. Remaining portions of the flow through fractions are stored at −20° C. Total E. coli extract or the purified proteins are solubilized in SDS sample buffer and subjected to PAGE according to standard procedures. Results of this procedure indicated the recombinant toxin fragment accounted for roughly 90% of the protein content of the sample.

The foregoing results indicates that the approach to creating MBP-L chain fusion proteins described herein could be used to efficiently produce wild-type and mutant recombinant BoNT/A-L chains. Further, the results demonstrate that recombinant L chains could be separated from the maltose binding domains of the fusion proteins and purified thereafter.

A sensitive antibody-based assay is developed to compare the enzymatic activities of recombinant L chain products and their native counterparts. The assay employed an antibody having specificity for the intact C-terminal region of SNAP-25 that corresponded to the BoNT/A cleavage site. Western Blotting of the reaction products of BoNT/A cleavage of SNAP-25 indicated an inability of the antibody to bind SNAP-25 sub-fragments. Thus, the antibody reneurotoxin employed in the following Example detected only intact SNAP-25. The loss of antibody. binding served as an indicator of SNAP-25 proteolysis mediated by added BoNT/A light chain or recombinant derivatives thereof.

EXAMPLE 7

Evaluation of the Proteolytic Activities of Recombinant

L Chains Against a SNAP-25 Substrate

This Example describes a method to demonstrate that both native and recombinant BoNT/A-L chains can proteolyze a SNAP-25 substrate. A quantitative assay is employed to compare the abilities of the wild-type and their recombinant analogs to cleave a SNAP-25 substrate. The substrate utilized for this assay is obtained by preparing a glutathione-S-transferase (GST)-SNAP-25 fusion protein, containing a cleavage site for thrombin, expressed using the pGEX-2T vector and purified by affinity chromatography on glutathione agarose. The SNAP-25 is then cleaved from the fusion protein using thrombin in 50 mM Tris-HCl (pH 7.5) containing 150 mM NaCl and 2.5 mM CaCl$_2$ (Smith et al., Gene 67:31 (1988)) at an enzyme:substrate ratio of 1:100. Uncleaved fusion protein and the cleaved glutathione- binding domain bound to the gel. The recombinant SNAP-25 protein is eluted with the latter buffer and dialyzed against 100 mM HEPES (pH 7.5) for 24 hours at 4° C. The total protein concentration is determined by routine methods.

Rabbit polyclonal antibodies specific for the C-terminal region of SNAP-25 are raised against a synthetic peptide having the amino acid sequence, CANQRATKMLGSG (SEQ ID#3). This peptide corresponded to residues 195 to 206 of the synaptic plasma membrane protein and an N-terminal cysteine residue not found in native SNAP-25. The synthetic peptide is conjugated to bovine serum albumin (BSA) (Sigma; Poole, UK) using maleimidobenzoyl-N-hydroxysuccinimide ester (MBS) as a cross-linking neurotoxin (Sigma; Poole, UK) to improve antigenicity (Liu et al., Biochemistry 18:690 (1979))1. Affinity purification of the anti-peptide antibodies is carried out using a column having the antigenic peptide conjugated via its N-terminal cysteine residue to an aminoalkyyl agarose resin (Bio-Rad; Hemel Hempstead, UK), activated with iodoacetic acid using the cross-linker ethyl 3-(3-dimethytpropyl) carbodiimide. After successive washes of the column with a buffer containing 25 mM Tris-HCl (pH 7.4) and 150 mM NaCl, the peptide-specific antibodies are eluted using a solution of 100 mM glycine (pH 2.5) and 200 mM NaCl, and collected in tubes containing 0.2 ml of 1 M Tris-HCl (pH 8.0) neutralizing buffer.

All recombinant preparations containing wild-type L chain are dialyzed overnight at 4° C. into 100 mM HEPES (pH 7.5) containing 0.02% Lubrol and 10 µM zinc acetate before assessing their enzymatic activities. BoNT/A, previously reduced with 20 mM DTT for 30 minutes at 37° C., as well as these dialyzed. samples, are then diluted to different concentrations in the latter HEPES buffer supplemented with 1 mM DTT.

Reaction mixtures include 5 µl recombinant SNAP-25 substrate (8.5 µM final concentration) and either 20 µl reduced BoNT/A or recombinant wild-type L chain. All samples are incubated at 37° C. for 1 hour before quenching the reactions with 25 µl aqueous 2% trifluoroacetic acid (TFA) and 5 mM EDTA (Foran et al., Biochemistry 33:15365(1994)). Aliquots of each sample are prepared for SDS-PAGE and Western blotting with the polyclonal SNAP-25 antibody by adding SDS-PAGE sample buffer and boiling. Anti-SNAP-25 antibody reactivity is monitored using an ECL detection system and quantified by densitometric scanning.

Western blotting results indicate clear differences between the proteolytic activities of the purified mutant L chain and either native or recombinant wild-type BoNT/A-L chain. Specifically, recombinant wild-type L chain cleaves the SNAP-25 substrate, though somewhat less efficiently than the reduced BoNT/A native L chain that serves as the positive control in the procedure. Thus, an enzymatically active form of the BoNT/A-L chain is produced by recombinant means and subsequently isolated. Moreover, substitution of a single amino acid in the L chain protein abrogated the ability of the recombinant protein to degrade the synaptic terminal protein.

As a preliminary test of the biological activity of the wild-type recombinant BoNT/A-L chain, the ability of the MBP-L chain fusion protein to diminish Ca$^{2+}$-evoked catecholamine release from digitonin-permeabilized bovine adrenochromaffin cells is examined. Consistently, wild-type recombinant L chain fusion protein, either intact or cleaved with Factor X$_2$ to produce a mixture containing free MBP and recombinant L chain, induced a dose-dependent inhibition of Ca$^{2+}$-stimulated release equivalent to the inhibition caused by native BoNT/A.

EXAMPLE 8

Reconstitution of Native L Chain. Recombinant Wild-Type L Chain with Purified H Chain Native H and L chains are dissociated from BoNT/A (List Biologicals Inc.; Campbell, USA) with 2 M urea, reduced with 100 mM DTT and then purified according to established chromatographic procedures (Kozaki et al., Japan *J. Med. Sci. Biol.* 34:61 (1981); Maisey et al., Eur. *J. Biochem.* 177:683 (1988)). Purified H chain is combined with an equimolar amount of either native L chain or recombinant wild-type L chain. Reconstitution is carried out by dialyzing the samples against a buffer consisting of 25 mM Tris (pH 8.0), 50 µM zinc acetate and 150 mM NaCl over 4 days at 4° C. Following dialysis, the association of the recombinant L chain and native H chain to form disulfide-linked-150 kDa dichains is monitored by SDS-PAGE and quantified by densitometric scanning. The proportion of dichain molecules formed with the recombinant L chains is lower than that obtained when native L chain is employed. Indeed, only about 30% of the recombinant wild-type or mutant L chain is reconstituted while >90% of the native L chain reassociated with the H chain. In spite of this lower efficiency of reconstitution, sufficient material incorporating the recombinant L chains is easily produced for use in subsequent functional studies.

While this invention has been described with respect to various specific examples and embodiments, it is to be understood that the invention is not limited thereto and that it can be variously practiced with the scope of the following claims. Other embodiments, versions, and modifications within the scope of the present invention are possible. For example, from about 500 units to about 4,000 units of a *botulinum* toxin type B can be used to treat an injured muscle according to the present disclosed invention.

We claim:

1. A method for facilitating healing in an injured muscle, the method comprising the steps of:
   (a) local administration of a therapeutically effective amount of a *botulinum* toxin to an injured muscle, wherein the injured muscle has an injury selected from the group of injuries consisting of contusions, lacerations, ischemia, strain and rupture; and
   (b) treating the injured muscle with a treatment selected from the group of treatments consisting of: resting the injured muscle; icing the injured muscle; compressing the injured muscle; elevating the injured muscle; applying ultrasound to the inured muscle; contacting the injured muscle with hyperbaric oxygen; administering nonsteriodal anti-inflammatory drugs to the injured muscle and carrying out reparative surgery upon the injured muscle, thereby facilitating healing of the injured muscle.

2. The method of claim 1, wherein the step of treating the injured muscle is taken prior to, in conjunction with or following the step of administering the *botulinum* toxin to the injured muscle.

3. The method of claim 1, wherein healing of the injured muscle takes place within four months after local administration of the *botulinum* toxin.

4. The method of claim 1, wherein the step of local administration is by intramuscular injection.

5. The method of claim 1, wherein the *botulinum* toxin is *botulinum* toxin type A, B, $C_1$, D, E, F or G.

6. The method of claim 1, wherein the *botulinum* toxin is effective to immobilize the injured muscle during at least phase 1 or phase 2 of a repair process of the injured muscle.

7. The method of claim 1 wherein the *botulinum* toxin substantially immobilizes the injured muscle.

8. A method for facilitating healing in an injured muscle, comprising the steps of:
  (a) administering locally, a therapeutically effective amount of *botulinum* toxin type A or B to an injured muscle, wherein the injured muscle has an injury selected from the group of injuries consisting of contusions, lacerations, ischemia, strain and rupture; and
  (b) treating the injured muscle with a treatment selected from the group of treatments consisting of: resting the injured muscle, icing the injured muscle, compressing the injured muscle, elevating the injured muscle, applying therapeutic ultrasound to the injured muscle, utilizing hyperbaric oxygen therapy, administering nonsteriodal anti-inflammatory drugs and providing reparative surgery to the injured muscle, thereby facilitating healing of the injured muscle.

9. The method of claim 8, wherein healing of the injured muscle is facilitated within four months after the local administration of the *botulinum* toxin type A or B.

10. The method of claim 8, wherein the step for treating the injured muscle is taken prior to, in conjunction with or following the step of administering the *botulinum* toxin type A or B to the injured muscle.

11. The method of claim 8, wherein the step of local administration is by intramuscular injection.

12. The method of claim 8 wherein the *botulinum* toxin type A or B substantially immobilizes the injured muscle.

13. The method of claim 8, wherein the *botulinum* toxin type A or B is effective to immobilize the injured muscle during at least phase 1 or phase 2 of a repair process of the injured muscle.

* * * * *

UNITED STATES PATENT AND TRADEMARK OFFICE
CERTIFICATE OF CORRECTION

PATENT NO.         : 7,468,188 B2
APPLICATION NO.    : 11/507708
DATED              : December 23, 2008
INVENTOR(S)        : Brooks et al.

It is certified that error appears in the above-identified patent and that said Letters Patent is hereby corrected as shown below:

In column 3, line 17, delete "including," and insert -- including --, therefor.

In column 5, line 37, delete "Irvinve," and insert -- Irvine, --, therefor.

In column 6, line 54, delete "the." and insert -- the --, therefor.

In column 8, line 57-65, delete ""$H_N$" means a fragment (preferably having a molecular weight of about 50 kDa) derived from the H chain of a Clostridial neurotoxin which is approximately equivalent to the amino terminal segment of the H chain, or the portion corresponding to that fragment in the intact in the H chain. It is believed to contain the portion of the natural or wild type clostridial neurotoxin involved in the translocation of the L chain across an intracellular endosomal membrane." and insert the same on Col. 8, Line 58, below "as H." as a new paragraph.

In column 8-9, line 65-67 and 1-5, delete "$H_c$" means a fragment (about 50 kDa) derived from the H chain of a clostridial neurotoxin which is approximately equivalent to the carboxyl terminal segment of the H chain, or the portion corresponding to that fragment in the intact H chain. It is believed to be immunogenic and to contain the portion of the natural or wild type Clostridial neurotoxin involved in high affinity, presynaptic binding to motor neurons." and insert the same on Col. 8, Line 66, below "membrane." as a new paragraph.

In column 10, line 6, delete "phagocycosis" and insert -- phagocytosis --, therefor.

In column 11, Table 1, line 24, delete "Phyllomedeusa" and insert -- Phyllomedusa --, therefor.

In column 13, Table 1, line 39, delete "Recpetors" and insert -- Receptors --, therefor.

In column 13, Table 1, line 40, delete "recpetors" and insert -- receptors --, therefor.

In column 14, line 10, delete "Enyzmes" and insert -- Enzymes --, therefor.

In column 14, line 24, delete "C1," and insert -- $C_1$, --, therefor.

In column 16, line 11, delete "tom" and insert -- torn --, therefor.

In column 19, line 17, delete "AAAGGCCTTTTGTTMTAAACAA" and insert -- AAAGGCCTTTTGTTAATAAACAA --, therefor.

UNITED STATES PATENT AND TRADEMARK OFFICE
CERTIFICATE OF CORRECTION

PATENT NO. : 7,468,188 B2
APPLICATION NO. : 11/507708
DATED : December 23, 2008
INVENTOR(S) : Brooks et al.

It is certified that error appears in the above-identified patent and that said Letters Patent is hereby corrected as shown below:

In column 19, line 40, delete "his" and insert -- this --, therefor.

In column 20, line 16-27, delete "Reactive bands on PVDF membranes (Pharmacia; Milton Keynes, UK) are visualized using an anti-rabbit immunoglobulin conjugated to horseradish peroxidase (Bio-Rad; Hemel Hempstead, UK) and the ECL detection system (Amersham, UK). Western blotting results confirmed the presence of the dominant fusion protein together with several faint bands corresponding to proteins of lower M.sub.r than the fully sized fusion protein. This observation suggested that limited degradation of the fusion protein occurred in the bacteria or during the isolation procedure. Neither the use of 1 mM nor 10 mM benzamidine (Sigma; Poole, UK) during the isolation procedure eliminated this proteolytic breakdown." and insert the same on Col. 20, Line 15, after "(1993)." as continuation of the same paragraph.

In column 21, line 41, delete "antibody." and insert -- antibody --, therefor.

In column 22, line 17, delete "aminoalkyyl" and insert -- aminoalkyl --, therefor.

In column 22, line 19, delete "dimethytpropyl" and insert -- dimethylpropyl --, therefor.

In column 22, line 31, delete "dialyzed." and insert -- dialyzed --, therefor.

In column 23, line 3, delete "Chain." and insert -- Chain, --, therefor.

In column 23, line 60, delete "linked-150" and insert -- linked 150 --, therefor.

Signed and Sealed this

Twenty-sixth Day of May, 2009

JOHN DOLL
*Acting Director of the United States Patent and Trademark Office*

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<221> NAME/KEY: primer_bind
<222> LOCATION: (1)...(23)
<223> OTHER INFORMATION: PCR primer

<400> SEQUENCE: 1 aaaggcctttt tgttaataaa caa                                      23

<210> SEQ ID NO 2
<211> LENGTH: 26
<212> TYPE: DNA
<213> ORGANISM: Artificial Sequence
<220> FEATURE:
<221> NAME/KEY: primer_bind
<222> LOCATION: (1)...(26)
<223> OTHER INFORMATION: PCR primer

<400> SEQUENCE: 2
ggaattctta cttattgtat ccttta                                    26

<210> SEQ ID NO 3
<211> LENGTH: 13
<212> TYPE: PRT
<213> ORGANISM: Artificial Sequence
<220> FEATURE:
<221> NAME/KEY: PEPTIDE
<222> LOCATION: (1)...(13)
<223> OTHER INFORMATION: Synthetic Peptide

<400> SEQUENCE: 3

Cys Ala Asn Gln Arg Ala Thr Lys Met Leu Gly Ser Gly
 1               5                  10
```